(12) United States Patent
Headley

(10) Patent No.: US 9,554,930 B2
(45) Date of Patent: Jan. 31, 2017

(54) POWERED MEDICAL DEVICE DEPLOYMENT SYSTEM

(71) Applicant: Cook Medical Technologies LLC, Bloomington, IN (US)

(72) Inventor: Josh Headley, Ellettsville, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 305 days.

(21) Appl. No.: 14/261,584

(22) Filed: Apr. 25, 2014

(65) Prior Publication Data

US 2015/0305901 A1   Oct. 29, 2015

(51) Int. Cl.
A61F 2/06    (2013.01)
A61F 2/966   (2013.01)
A61F 2/95    (2013.01)

(52) U.S. Cl.
CPC ........ *A61F 2/966* (2013.01); *A61F 2002/9517* (2013.01)

(58) Field of Classification Search
CPC ........ A61F 2/2427; A61F 2/2436; A61F 2/95; A61F 2/954; A61F 2/962; A61F 2/966; A61F 2002/011; A61F 2002/9517; A61F 2002/9528; A61F 2002/9534
See application file for complete search history.

(56) References Cited

U.S. PATENT DOCUMENTS

| | | |
|---|---|---|
| 3,835,854 A | 9/1974 | Jewett |
| 3,838,688 A | 10/1974 | May et al. |
| 5,364,198 A | 11/1994 | Skenderi |
| 5,391,172 A | 2/1995 | Williams et al. |
| 6,402,760 B1 | 6/2002 | Fedida |
| 6,786,865 B2 | 9/2004 | Dhindsa |
| 6,974,465 B2 | 12/2005 | Belef et al. |
| 7,097,648 B1 | 8/2006 | Globerman et al. |
| 7,278,998 B2 | 10/2007 | Gaschino et al. |
| 7,285,130 B2 | 10/2007 | Austin |
| 7,686,816 B2 | 3/2010 | Belef et al. |
| 7,766,856 B2 | 8/2010 | Ferry et al. |
| 7,887,549 B2 | 2/2011 | Wenderow et al. |
| 7,967,829 B2 | 6/2011 | Gunderson et al. |
| 8,114,032 B2 | 2/2012 | Ferry et al. |
| 8,585,747 B2 | 11/2013 | Andreas et al. |

(Continued)

FOREIGN PATENT DOCUMENTS

| | | |
|---|---|---|
| EP | 2359776 | 12/2006 |
| EP | 1696827 | 5/2012 |

(Continued)

OTHER PUBLICATIONS

Cook Medical Incorporated, Celect Vena Cava Filter [Brochure]. 2009, pp. 1-2.

*Primary Examiner* — Melanie Tyson
(74) *Attorney, Agent, or Firm* — Buchanan Nipper

(57) ABSTRACT

Powered medical device deployment systems and methods are described herein. An embodiment of a powered medical device deployment system has a housing, a cannula, a sheath slidably disposed over the cannula, a flush port, a trigger, a drive mechanism, and a medical device. The drive mechanism is moveable between an on state and an off state. When the drive mechanism is in the on state the sheath is axially advanced over the cannula such that the medical device can be deployed at a point of treatment.

20 Claims, 7 Drawing Sheets

(56) References Cited

U.S. PATENT DOCUMENTS

| | | | |
|---|---|---|---|
| 2002/0177789 A1 | 11/2002 | Ferry et al. | |
| 2005/0080476 A1 | 4/2005 | Gunderson et al. | |
| 2005/0149159 A1* | 7/2005 | Andreas | A61F 2/95 623/1.11 |
| 2005/0177182 A1 | 8/2005 | van der Burg et al. | |
| 2006/0286145 A1 | 12/2006 | Horan et al. | |
| 2009/0024133 A1 | 1/2009 | Keady et al. | |
| 2011/0054585 A1 | 3/2011 | Osborne | |
| 2012/0022632 A1* | 1/2012 | Hoffman | A61F 2/966 623/1.11 |
| 2012/0239142 A1 | 9/2012 | Liu et al. | |
| 2013/0152941 A1 | 6/2013 | Nguyen et al. | |
| 2015/0088163 A1* | 3/2015 | George | A61B 17/0469 606/138 |

FOREIGN PATENT DOCUMENTS

| | | |
|---|---|---|
| EP | 2559388 | 2/2013 |
| EP | 2604198 | 6/2013 |
| WO | 9904728 | 2/1999 |
| WO | 03062672 | 7/2003 |
| WO | 2007022395 | 2/2007 |
| WO | 2008124844 | 10/2008 |
| WO | 2009009617 | 1/2009 |
| WO | 2011034754 | 3/2011 |
| WO | 2012116368 | 8/2012 |

\* cited by examiner

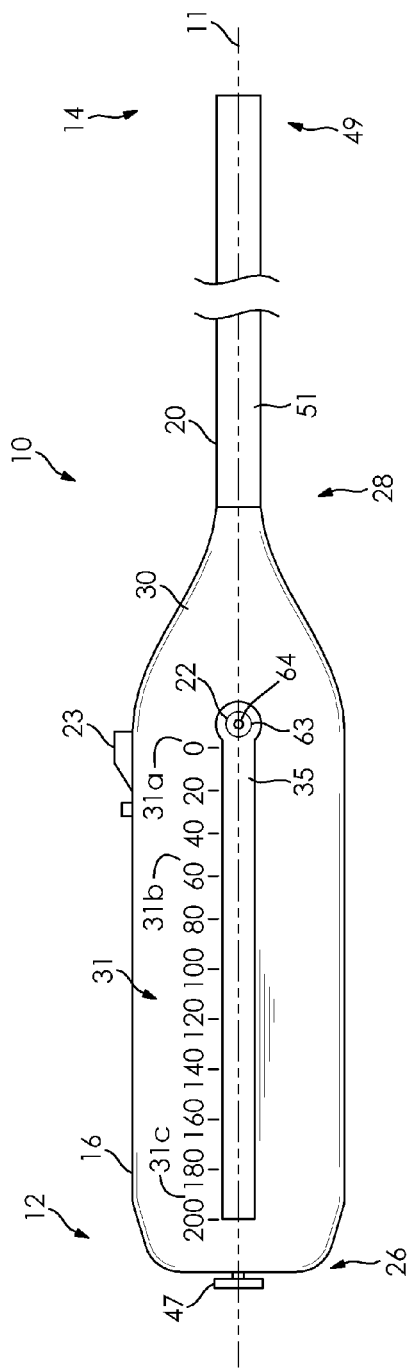
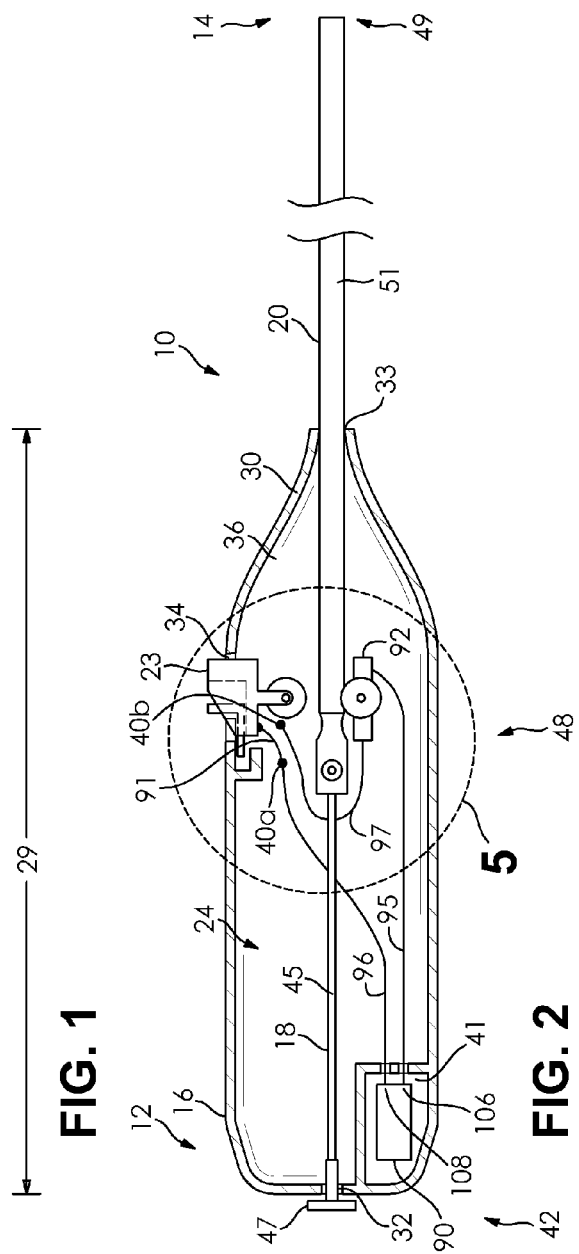
FIG. 1
FIG. 2

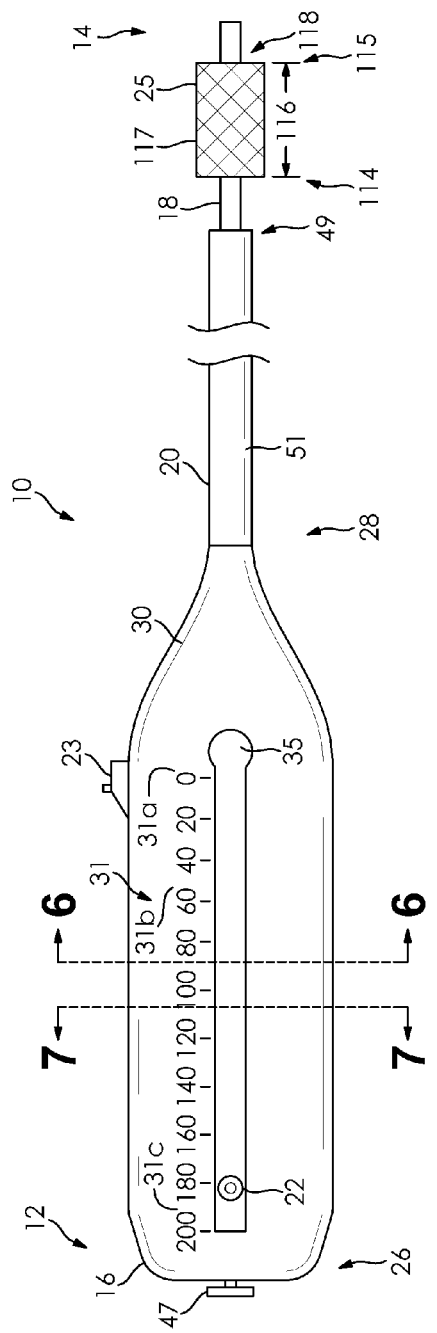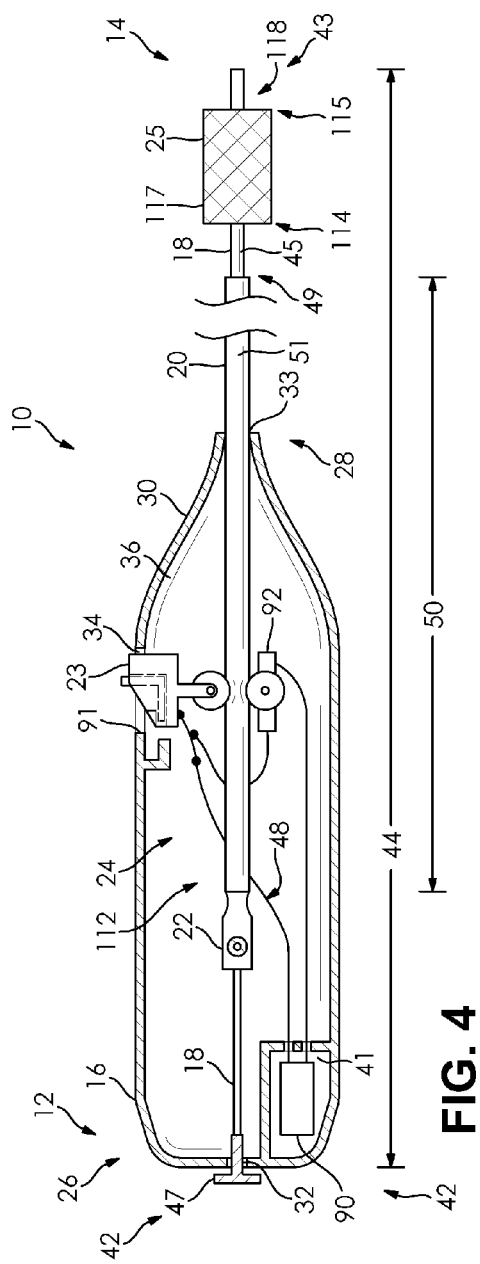

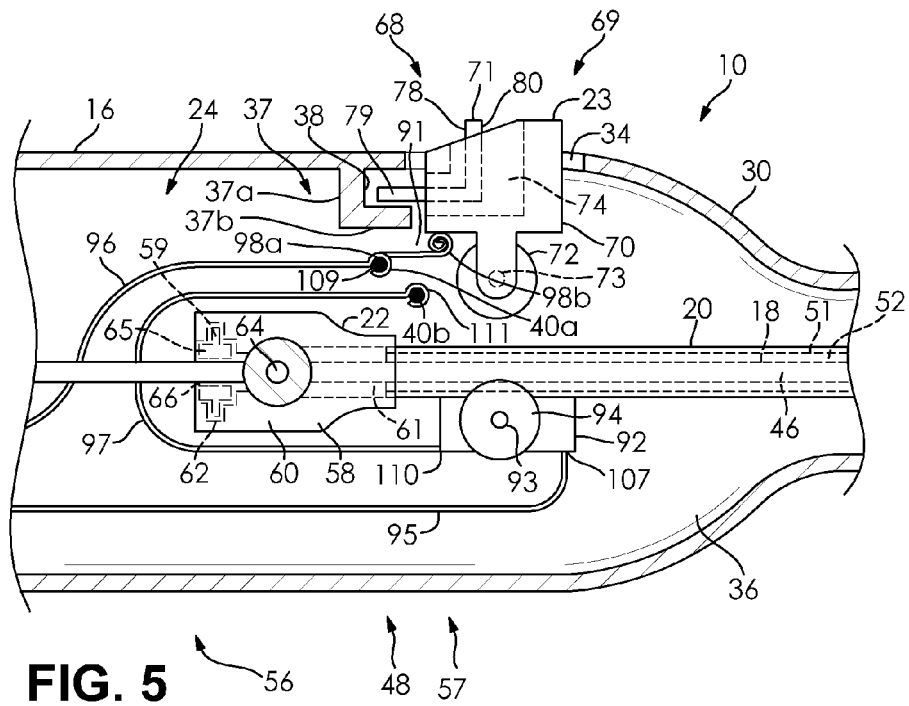
FIG. 5
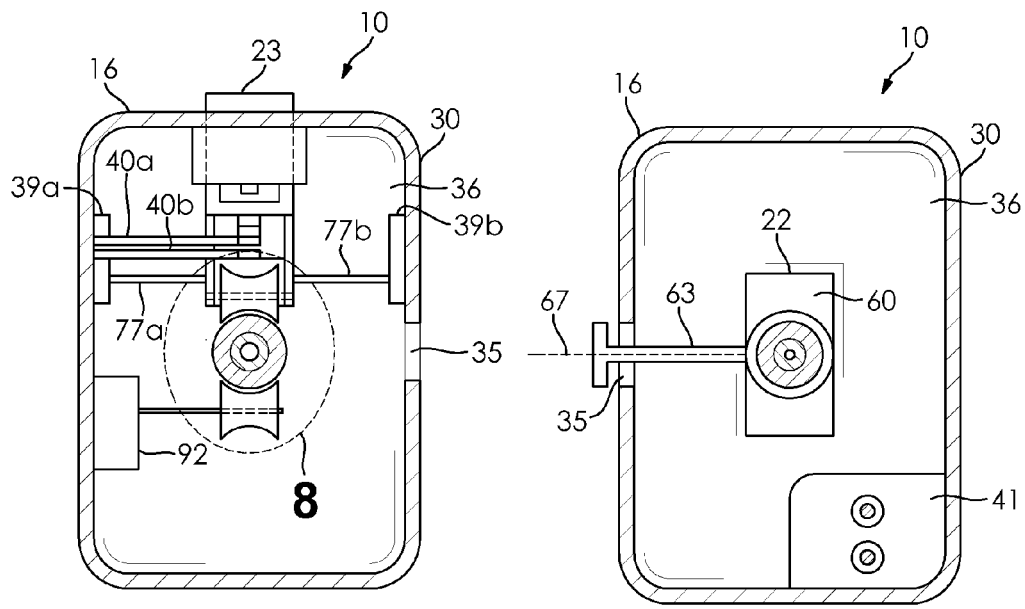
FIG. 6  FIG. 7

POWERED MEDICAL DEVICE DEPLOYMENT SYSTEM

DESCRIPTION OF FIGURES

FIG. 1 is a side view of a powered medical device deployment system in an extended configuration.

FIG. 2 is a partial cross-sectional view of the powered medical device deployment system illustrated in FIG. 1.

FIG. 3 is a side view of the powered medical device deployment system illustrated in FIG. 1 in a retracted configuration.

FIG. 4 is a partial cross-sectional view of the powered medical device deployment system illustrated in FIG. 3.

FIG. 5 is magnified view of area 5 illustrated in FIG. 2.

FIG. 6 is a cross-sectional view of the powered medical device deployment system illustrated in FIG. 3, taken along line 6-6. FIG. 6 omits the inclusion of the first wire member, the second wire member, and third wire member for clarity.

FIG. 7 is a cross-sectional view of the powered medical device deployment system illustrated in FIG. 3, taken along line 7-7.

DESCRIPTION OF EMBODIMENTS

Figure 8:
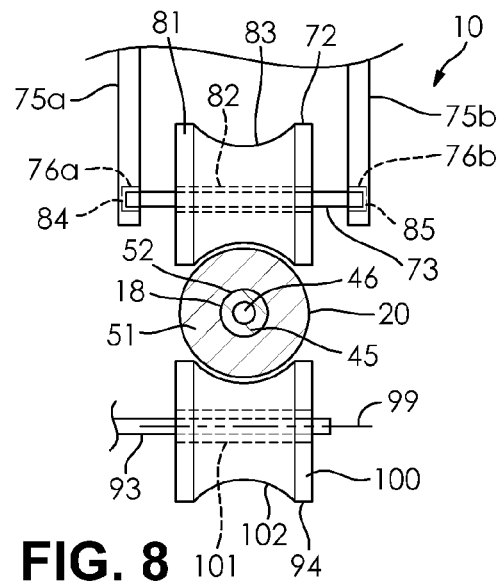
FIG. 8 is a magnified view of area 8 illustrated in FIG. 6.

The following detailed description and the appended drawings describe and illustrate various example embodiments of powered medical device deployment systems and methods of treatment. The description and illustration of these examples are provided to enable one skilled in the art to make and use a powered medical device deployment system and to practice a method of treatment using a powered medical device deployment system. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature. The use of "circumference" refers to the distance around the exterior surface of a body, element, or feature, and does not impart any structural configuration on the body, elements, or feature. The use of "bodily passage" or "body passage" refers to any passage within the body of an animal, including humans, and includes elongate passages, arteries, and veins.

The use of "motor" refers to any device capable of receiving energy (e.g., electrical energy) and producing movement, such as rotational movement. The use of "pancake motor" refers to any motor that has a thickness that is less than its length, width, and/or diameter (e.g., thin profile) and includes printed armature motors and servodisc motors.

FIGS. 1, 2, 3, 4, 5, 6, 7, and 8 illustrate an embodiment of a powered medical device deployment system 10 that has a lengthwise axis 11, a proximal end 12, a distal end 14, a housing 16, a cannula 18, a sheath 20, a flush port 22, a trigger 23, a drive mechanism 24, and a medical device 25. The powered medical device deployment system 10 has an extended configuration, illustrated in FIGS. 1, 2, and 5, and a retracted configuration, illustrated in FIGS. 3, 4, 6, 7, and 8. Movement of the powered medical device deployment system 10 between the extended configuration and the retracted configuration is described in more detail herein.

In the embodiment illustrated, the housing 16 has a proximal end 26, a distal end 28, an axial length 29, a housing body 30, and a plurality of indicia 31. The axial length 29 of the housing 16 extends from the proximal end 26 to the distal end 28 of the housing 16. The housing body 30 defines a first opening 32, a second opening 33, a third opening 34, a slot 35, a chamber 36, a flange 37, a recess 38, a first track 39a, a second track 39b, a first pin 40a, a second pin 40b, and an energy storage chamber 41.

Each of the first opening 32, the second opening 33, the third opening 34, and the slot 35 extends through the housing body 30 and provides access to the chamber 36. Each of the first opening 32 and second opening 33 is disposed on an axis that extends through the housing 16 (e.g., lengthwise axis 11). However, alternative embodiments can include a first opening and a second opening that are disposed on different axes. The first opening 32 provides access to the lumen 46 defined by the cannula 18 and is sized and configured to receive a portion of the cannula 18. The second opening 33 is sized and configured to receive a portion of the cannula 18 and the sheath 20. The third opening 34 is defined between the proximal end 26 and the distal end 28 of the housing 16 and is sized and configured to receive a portion of the trigger 23. While the third opening 34 has been illustrated as positioned between the proximal end 26 and the distal end 28 of the housing 16, the third opening defined by a housing can be positioned at any suitable location on a housing, such as on the proximal end or the distal end of the housing.

The slot 35 is disposed between the proximal end 26 and the distal end 28 of the housing 16 and extends along a portion of the axial length 29 of the housing 16. In the illustrated embodiment, the slot 35 is defined on an axis that is parallel to the lengthwise axis 11 of the powered medical device deployment system 10. However, a slot can be defined on an axis that is disposed at any suitable angle to the lengthwise axis of a powered medical device deployment system. The slot 35 is sized and configured to receive a portion of the flush port 22.

As best illustrated in FIG. 5, the flange 37 has a first portion 37a that extends into the chamber 36 define by the housing 16 and a second portion 37b that extends toward the distal end 28 of the housing 16 such that the recess 38 is formed between the interior surface of the housing 16 and the flange 37. Optionally, a housing can omit the inclusion of a flange (e.g., in embodiments in which a safety release is omitted from a trigger).

As best illustrated in FIG. 6, each of the first track 39a and the second track 39b extends into the chamber 36 and is sized and configured to receive a portion of the trigger 23 such that the trigger 23 can be moved between a first position and a second position, as described in more detail herein. For example, the first track 39a is sized and configured to receive a portion of the first pin 77a defined by the trigger body 70 and the second track 39b is sized and configured to receive a portion of the second pin 77b defined by the trigger body 70. Each of the first track 39a and the second track 39b has a lengthwise axis that is disposed on a plane that extends through the lengthwise axis 11 of the powered medical device deployment system 10. Optionally, a housing can define a single track or more than two tracks and/or include a spring one or more tracks such that the trigger 23 is biased toward its first position.

Each of the first pin 40a and the second pin 40b extends into the chamber 36 from the interior wall. In the illustrated embodiment, the first pin 40a is disposed on a first axis and the second pin 40b is disposed on a second axis. Each of the first axis and the second axis is disposed between the trigger 23 and the cannula 18. This configuration provides a mechanism for moving the drive mechanism 24 between an on state and an off state, as described in more detail herein. However, alternative embodiments can position a first pin and a second pin at any suitable location within the chamber of a housing, such as positioning a first pin on a first axis and/or a second pin on a second axis such that each of the first axis and the second axis pass through the lengthwise axis of the powered medical device deployment system.

In the illustrated embodiment, the energy storage chamber 41 is defined near the proximal end 26 of the housing 16 and is sized and configured to receive an energy storage device, such as energy storage device 90. An alternative embodiment can include a housing that defines a track that is adapted to receive a portion of a removable sleeve that covers the energy storage chamber such that any energy storage device housed within the energy storage chamber can be replaced. While energy storage chamber 41 has been illustrated as defined near the proximal end 26 of the housing 16, an energy storage chamber can be defined at any suitable location on the housing of a powered medical device deployment system, such as at the proximal end of the housing, between the proximal end and the distal end of the housing, or at the distal end of the housing.

The plurality of indicia 31 is disposed on the exterior surface of the housing 16 and adjacent to the slot 35. In the embodiment illustrated, each indicium of the plurality of indicia 31 is disposed on an axis that is parallel to the slot 35. However, a plurality of indicia can be disposed in any suitable configuration along the axial length of the slot 35. A first indicium 31a of the plurality of indicia 31 is disposed a first distance from a second indicium 31b of the plurality of indicia 31 and a third indicium 31c of the plurality of indicia 31 is disposed a second distance from the second indicium 31b of the plurality of indicia 31. The first distance is less than the second distance. In the illustrated embodiment, each indicium of the plurality of indicia 31 is disposed at an equal distance from another indicium of the plurality of indicia 31.

Each indicium of the plurality of indicia 31 has a form that corresponds to a nominal value of a length (e.g., length equal to the distance between the distal end 43 of the cannula 18 and the distal end 49 of the sheath 20, length equal to the length of the medical device 25 disposed distal to the distal end 49 of the sheath 20). In the illustrated embodiment, the first indicium 31a of the plurality of indicia 31 has a form that corresponds to the nominal value of a first length (e.g., zero) when the distal end 43 of the cannula 18 is disposed adjacent to the distal end 49 of the sheath 20. The second indicium 31b of the plurality of indicia 31 has a form that corresponds to the nominal value of a second length that is greater than the first length. The second length is equal to the distance between the distal end 43 of the cannula 18 and the distal end 49 of the sheath 20 when the sheath 20 has been retracted, as described in more detail herein. The third indicium 31c of the plurality of indicia 31 has a form that corresponds to the nominal value of a third length that is greater than the second length. The third length is equal to the distance between the distal end 43 of the cannula 18 and the distal end 49 of the sheath 20 when the sheath 20 has been retracted, as described in more detail herein. Thus, each indicium of the plurality of indicia 31 expresses a length that is equal to the distance between the distal end 43 of the cannula 18 and the distal end 49 of the sheath 20. The inclusion of a plurality of indicia 31 on the exterior surface of the housing 16 provides a mechanism for determining the distance the sheath 20 has been retracted from the cannula 18.

While the nominal value of the lengths formed by each indicium of the plurality of indicium has been described as a length that is equal to the distance between the distal end 43 of the cannula 18 and the distal end 49 of the sheath 20, each indicium of a plurality of indicia can have a form that corresponds to a length equal to any suitable relative distance. For example, an alternative embodiment can include a plurality of indicia, in addition to or alternative to those described above, such that each indicium of the plurality of indicia has a form that corresponds to a nominal value of a length equal to the length of the medical device 25 that is disposed distal to the distal end 49 of the sheath 20 (e.g., the length of the medical device 25 that has been deployed).

The form of each indicium of the plurality of indicia 31 can be based on any suitable unit of length, and skilled artisans will be able to select a suitable unit of length to base the form of an indicium according to a particular embodiment based on various considerations, including the length of a cannula, the length of a sheath, and/or the length of a medial device. Example units of length considered suitable to base the form of an indicium include, but are not limited to, United States customary units, the Metric System, the International System of Units, and any other unit of length considered suitable for a particular application.

While each indicium of the plurality of indicia 31 disposed on housing 16 has been illustrated as disposed at an equal distance from another indicium of the plurality of indicia 31, any suitable distance can be disposed between each indicium of a plurality of indicia and another indicium of the plurality of indicia. Skilled artisans will be able to select a suitable distance between each indicium of a plurality of indicia and another indicium of the plurality of indicia according to a particular embodiment based on various considerations, including length of the sheath relative to the length of the cannula and/or the length of the medical device being deployed from the system. Example distances considered suitable between each indicium of a plurality of indicia and another indicium of the plurality of indicia include distances that are equal, or substantially equal, to one another, distances that vary from one another, a first distance that is equal to the length of a first stage of the deployment of a medical device, a distance that is equal to the length of a second stage of the deployment of a medical device, a distance that is equal to the length of a third stage of the deployment of a medical device, and any other distance considered suitable for a particular application.

Each indicium of the plurality of indicia 31 can be formed using any suitable technique. For example, each indicium of the plurality of indicia 31 can be formed from the housing body 30 (e.g., raised protuberance extending outward from housing body, recess extending inward from exterior surface), or be embedded within the material that forms the housing 16. Alternatively, each indicium of the plurality of indicia 31 can be formed by applying ink to the exterior surface of the housing 16.

The housing 16 can be formed of any suitable material and using any suitable manufacturing technique, and skilled artisans will be able to select a suitable material and technique to form a housing according to a particular embodiment based on various considerations, including the material (s) that forms the cannula and/or sheath of an embodiment. Example materials considered suitable to form a housing include biocompatible materials, materials that can be made biocompatible, metals such as stainless steel, titanium, nickel-titanium alloys, polymers, polyethylene, polyvinyl chloride, polystyrene, and any other material considered suitable for a particular application. Example techniques considered suitable to form a housing include injection molding, casting, and any other technique considered suitable for a particular application. For example, the housing can be formed as two separate elements that cooperatively define the various elements and features described herein (e.g., chamber 36) and can be attached to one another using any suitable technique, such as using threaded components, or method, such as using adhesive.

While the housing 16 and chamber 36 have been illustrated as having a particular structural configuration, a housing and the chamber defined by the housing body can have any suitable size, shape, and configuration, and the illustrated housing and chamber are merely examples of a suitable housing and chamber. For example, a housing, or each portion of a housing, can be formed such that it is a solid piece, or pieces, that define one or more recesses that are sized and configured to house the various elements and components described herein.

In the illustrated embodiment, the cannula 18 is partially disposed within the chamber 36 and has a proximal end 42, a distal end 43, an axial length 44, and a cannula body 45. The axial length 44 of the cannula 18 extends from the proximal end 42 to the distal end 43 of the cannula 18. The cannula body 45 defines a lumen 46 that extends through the cannula 18 from the proximal end 42 to the distal end 44 of the cannula 18.

The proximal end 42 of the cannula 18 is disposed proximal to the proximal end 26 of the housing 16 and the distal end 43 of the cannula 18 is disposed outside of the chamber 36 and distal to the distal end 28 of the housing 16. Thus, in the embodiment illustrated, the housing 16 is disposed between the proximal end 42 and the distal end 43 of the cannula 18. However, other embodiments can include a cannula that has a proximal end disposed at the proximal end of the housing, a proximal end disposed between the proximal end and the distal end of the housing (e.g., within the chamber defined by the housing), or at any other suitable location. Alternative embodiments can include a cannula that has a first portion of the axial length of the cannula that is entirely disposed, or partially disposed, within the housing and a second portion of the axial length of the cannula that is disposed outside of, or partially disposed within, the housing. The first portion can be formed of a first material (e.g., metal) and the second portion can be formed of a second material (e.g., polymer) that is relatively more flexible than the first material. This arrangement provides a flexible cannula along the second portion that can be navigated through tortuous anatomy. The first portion can be attached to the second portion using any suitable method or technique, such as those described herein (e.g., bonding), capable of providing a sealed engagement (e.g., leak free) between the first portion and the second portion.

A connector 47 is attached to the proximal end 42 of the cannula 18 and provides a mechanism for attaching another device, such as an irrigation device, to the cannula 18 such that the device is in communication with the lumen 46 defined by the cannula 18. The connector 47 can comprise any suitable connector or adapter capable of attaching one or more devices to the cannula 18. Skilled artisans will be able to select a suitable connector or adapter to include on a cannula according to a particular embodiment based on various considerations, including the material(s) that forms the cannula. Example connectors or adapters considered suitable to include on a cannula include threaded connectors, Tuohy Borst adapters, luer lock connectors, conical connectors (e.g., cones, sockets), and any other connector or adapter considered suitable for a particular application.

In the illustrated embodiment, the sheath 20 is partially disposed within the chamber 36 and is slidably disposed over the cannula 18 such that it can move axially over the cannula 18. The sheath 20 has a proximal end 48, a distal end 49, an axial length 50, and a sheath body 51. The axial length 50 of the sheath 20 extends from the proximal end 48 to the distal end 49 of the sheath 20. The sheath body 51 defines a lumen 52 that extends through the sheath 20 from the proximal end 49 to the distal end 50 of the sheath 20. The proximal end 48 of the sheath 20 is disposed within the chamber 36 and the distal end 49 of the sheath 20 is disposed outside of the chamber 36 and distal to the distal end 28 of the housing 16. The axial length 50 of the sheath 20 is less than the axial length 44 of the cannula 18.

The cannula 18, sheath 20, and connector 47 can be formed of any suitable material and using any suitable manufacturing technique, and skilled artisans will be able to select a suitable material and technique to form a cannula, sheath, and/or connector according to a particular embodiment based on various considerations, including the material (s) that forms the housing of an embodiment. Example materials considered suitable to form a cannula, sheath, and/or connector include biocompatible materials, materials that can be made biocompatible, metals such as stainless steel, titanium, nickel-titanium alloys, polymers, polyethylene, polyvinyl chloride, polystyrene, and any other material considered suitable for a particular embodiment. For example, the cannula of an embodiment can be formed of a first material and the sheath of the embodiment can be formed of a second material that is the same as, or different than, the first material. The second material can be relatively more flexible than the first material. Example techniques considered suitable to form a cannula, sheath, and/or connector include injection molding, casting, and any other technique considered suitable for a particular embodiment.

In the illustrated embodiment, the flush port 22 is attached to the sheath 20, is disposed within the chamber 36, and is slidably disposed over the cannula 18 such that it can move axially over the cannula 18. In the embodiment shown, the flush port 22 is attached to the distal end 49 of the sheath 20. However, alternative embodiments can include a flush port that is attached between the proximal end and the distal end of the sheath. The flush port 22 has a proximal end 56, a distal end 57, a flush port body 58, and a sealing member 59. The flush port body 58 defines a guide member 60, a first lumen 61, a recess 62, a port 63, and a second lumen 64.

The first lumen 61 extends through the guide member 60 from the proximal end 56 to the distal end 57 of the flush port 22 and has a proximal portion that is sized and configured to receive a portion of the cannula 18 and a distal portion that is sized and configured to receive a portion of the cannula 18 and the sheath 20. Depending on the placement of a flush port on a sheath, alternative embodiments can include a flush port that has a first lumen that is sized and configured to receive a portion of the cannula or a portion of the sheath. The recess 62 is disposed between the proximal end and the distal end of the first lumen 61 and extends outward from the lengthwise axis of the flush port 22 and about the circumference of the first lumen 61. The recess 62 is sized and configured to receive a portion of the sealing member 59. Alternatively, the recess can be sized and configured to receive the entire sealing member.

While the recess 62 has been illustrated as defined between the proximal end and the distal end of the first lumen 61, alternative embodiments can include a recess that is define at any other suitable location on a flush port. For example, a recess can be defined on the proximal end and/or the distal end of the flush port and be sized and configured to receive a portion, or the entirety of a sealing member. In embodiments in which a recess is defined on both the proximal end and the distal end of a flush port, the flush port can include a first sealing member disposed within the first recess and/or a second sealing member disposed within the second recess.

The sealing member 59 has a sealing member body 65 that defines a lumen 66 that is sized and configured to receive a portion of the cannula 18. The sealing member 59 is disposed within the recess 62 defined by the flush port body 58 and the cannula 18 is disposed through the lumen 66 defined by the sealing member 59. The sealing member 59 can comprise any suitable structure and be formed of any suitable material capable of providing a moveable sealing engagement between the flush port 22 and the cannula 18 such that the sealing member 59 is moveable along the cannula 18. Skilled artisans will be able to select a suitable structure and material to form a sealing member according to a particular embodiment based on various considerations, including the material(s) that forms the cannula and/or the sheath. Example materials considered suitable to form a sealing member include elastomers, polymers, polytetrafluoroethylene (ePFTE), nylon, polyethylene, silicone, urethane, and any other material considered suitable for a particular embodiment. Example structures considered suitable for a sealing member include structures that define an outside diameter that is equal to, substantially equal to, or greater than the diameter of the recess defined by the flush port body such that a snap fit configuration can be accomplished between the sealing member and the flush port. The sealing member 59 can be attached to the flush port 22 using any suitable method, such as using an adhesive.

The port 63 extends from the guide member 60 and away from the lengthwise axis 11 of the powered medical device deployment system 10 and extends through the slot 35 defined by the housing 16. The second lumen 64 extends through the port 63 and is in communication with the first lumen 61 such that the junction between the first lumen 61 and the second lumen 64 is disposed distal to the distal end 49 of the sheath 20. Alternatively, the junction between the first lumen and the second lumen can be defined between the proximal end and the distal end of the sheath. In this embodiment, the sheath can define an opening that provides access to the lumen defined by the sheath and can optionally include a sealing member on the proximal end of the sheath. The second lumen 64 is disposed on an axis 67 that extends through the slot 35 defined by the housing 16. Alternative embodiments can include a port that does not extend through the slot defined by a housing such that the entire port is disposed within the chamber defined by the housing. In these alternative embodiments, the second lumen can be defined on an axis that extends through the slot defined by the housing.

The flush port 22 can be attached to the sheath 20 using any suitable technique or method, and skilled artisans will be able to select a suitable technique or method to attach a flush port to a sheath according to a particular embodiment based on various considerations, including the material(s) that forms the sheath and/or flush port. Example techniques and methods considered suitable to attach a sheath to a flush port include using mechanical connections, threaded connections, welding, fusing (e.g., heat fusing), using adhesives, and any other technique or method considered suitable for a particular application.

The flush port 22 can be formed of any suitable material and using any suitable manufacturing technique, and skilled artisans will be able to select a suitable material and technique to form a flush port according to a particular embodiment based on various considerations, including the material (s) that forms the cannula and/or sheath of an embodiment. Example materials considered suitable to form a flush port include biocompatible materials, materials that can be made biocompatible, metals such as stainless steel, titanium, nickel-titanium alloys, polymers, polyethylene, polyvinyl chloride, polystyrene, and any other material considered suitable for a particular embodiment. Example techniques considered suitable to form a flush port include injection molding, casting, and any other technique considered suitable for a particular application. In the embodiment illustrated, the flush port 22 is formed of a first material and the sealing member 59 is formed of a second material that is the same as, or different from, the first material but is relatively more flexible than the first material. However, a sealing member can alternatively be formed of a material that has the same flexibility as the material that forms the flush port.

In the illustrated embodiment, the trigger 23 is disposed through the third opening 34 defined by the housing 16 and is partially disposed within the chamber 36. The trigger 23 is moveable between a first position and a second position. The trigger 23 has a proximal end 68, a distal end 69, a trigger body 70, a safety release 71, an idler wheel 72, and an axle 73. The trigger body 70 defines a passageway 74, a first protuberance 75a, a second protuberance 75b, a first recess 76a, a second recess 76b, a first pin 77a, and a second pin 77b.

The passageway 74 extends through the trigger body 70 such that a first end of the passageway 74 provides access to the environment exterior to the chamber 36 defined by the housing 16 and the second end of the passageway 74 is directed toward the recess 38 defined by the housing 16 when the trigger 23 is in the first position. The passageway 74 is sized and configured to receive a portion of the safety release 71 and provides a mechanism for retaining the safety release 71 on the flush port 22. As best illustrated in FIG. 8, each of the first protuberance 75a and second protuberance 75b extends away from the third opening 34 defined by the housing 16 a distance that is greater than the radius of the idler wheel 72. The first recess 76a is defined on the first protuberance 75a and is directed toward the second protuberance 75b. The second recess 76b is defined on the second protuberance 75b and is directed toward the first protuberance 75a.

In the embodiment illustrated, the safety release 71 is partially disposed within the passageway 74 defined by the trigger 23 and is moveable between a first position and a second position. The safety release 71 has a safety release body 78 that defines a locking member 79 and a protuberance 80 that extends from the locking member 79 at an angle. The safety release 71 is disposed within the passageway 74 defined by the trigger body 70 such that the protuberance 80 extends beyond the outer surface of the trigger 23, toward the environment exterior to the chamber 36, and can be manipulated by a user to move the safety release 71 between its first position and second position. In the first position, the protuberance 80 is disposed near the proximal end 68 of the trigger 23 and the locking member 79 extends beyond the outer surface of the trigger 23 and into the recess 38 defined by the housing 16. In the first position, the trigger 23 is prevented from moving into the chamber 36 beyond where the locking member 79 contacts the flange 37. In the second position, the protuberance 80 is disposed distal to the first position and the locking member 79 is free of the recess 38 defined by the housing 16. In the second position, the trigger 23 can be moved into the chamber 36 until the first and second pins 77a, 77b contact the end of the first and second tracks 39a, 39b. Alternative embodiments can omit the inclusion of a passageway (e.g., passageway 74) and a safety release (e.g., safety release 71). Optionally, a spring can be disposed between the safety release and the trigger body such that the safety release is biased toward its first position.

The idler wheel 72 has an idler wheel body 81 that defines a passageway 82 and a concave surface 83 about the circumference of the idler wheel 72. The idler wheel 72 is free of contact with the sheath 20 when the trigger 23 is in the first position, as illustrated in FIG. 5. The idler wheel 72 contacts the sheath 20 when the trigger 23 is in the second position, as illustrated in FIGS. 6 and 8. Alternative embodiments can include an idler wheel that contacts the sheath when the trigger is in the first position. The idler wheel 72 can be formed of any suitable material, such as biocompatible materials, materials that can be made biocompatible, metals such as stainless steel, titanium, nickel-titanium alloys, polymers, polyethylene, polyvinyl chloride, polystyrene, and any other material considered suitable for a particular embodiment. Optionally, an idler wheel, or a portion of the idler wheel (e.g., concave surface 83), can be formed of a high friction material(s) (e.g., neoprene) such that a high coefficient of friction is created between the idler wheel and the sheath relative to embodiments that form an idler wheel of a low friction material(s). Optionally, a portion of the idler wheel (e.g., concave surface) can include a coating that increases the coefficient of friction between the idler wheel and the exterior surface of the sheath relative to embodiments that do not include a coating.

The axle 73 is disposed through the passageway 82 defined by the idler wheel 72 and has a first end 84 rotatably disposed within the first recess 76a and a second end 85 rotatably disposed within the second recess 76b. Alternatively, an axle can be fixedly attached within the first recess and second recess such that the idler wheel can rotate about the axle.

The trigger 23 can be formed of any suitable material and using any suitable manufacturing technique, and skilled artisans will be able to select a suitable material and technique to form a trigger according to a particular embodiment based on various considerations, including the material(s) that forms the housing of an embodiment. Example materials considered suitable to form a trigger include biocompatible materials, materials that can be made biocompatible, metals such as stainless steel, titanium, nickel-titanium alloys, polymers, polyethylene, polyvinyl chloride, polystyrene, and any other material considered suitable for a particular embodiment. Example techniques considered suitable to form a trigger include injection molding, casting, and any other technique considered suitable for a particular embodiment. Optionally, a trigger can be formed of two portions that can be attached to one another such that when they are combined they cooperatively define a passageway, such as passageway 74.

In the illustrated embodiment, the drive mechanism 24 is disposed within the chamber 36 defined by the housing 16 and is configured to move the sheath 20 axially over the cannula 18. The drive mechanism 24 comprises an energy storage device 90, a spring 91, a motor 92, a drive axle 93, a drive wheel 94, a first wire member 95, a second wire member 96, and a third wire member 97. The drive mechanism 24 is adapted to move between an on state and an off state such that when the drive mechanism 24 is in the on state the sheath 20 and the flush port 22 move axially over the cannula 18 and the axis 67 that extends through the slot 35 defined by the housing 16 moves within the slot 35. When the drive mechanism 24 is in the off state, the sheath 20 is static relative to the cannula 18.

The energy storage device 90 is disposed within the energy storage chamber 41 defined by the housing 16 and is configured to store energy. The energy storage device 90 is in communication with the motor 92 via the spring 91, the first wire member 95, the second wire member 96, and the third wire member 97, as described in more detail herein. Optionally, a non-conductive member (e.g., removable pull-tab) can be positioned between the energy storage device 90 and the first wire member 95 and the second wire member 96 such that the motor 92 is unable to move between its on state and off state until the non-conductive member is removed. Optionally, an energy storage device can be omitted from a powered medical device deployment system. For example, an external power source can be attached to a drive mechanism (e.g., first wire member, second wire member) such that a motor can be moved between its on state and off state.

The energy storage device 90 can comprise any suitable energy storage device capable of storing electrical energy and providing electrical energy to the motor 92, and skilled artisans will be able to select a suitable energy storage device to include in a powered medical device deployment system according to a particular embodiment based on various considerations, including the type of motor included in the powered medical device deployment system. Example energy storage devices considered suitable to include in a powered medical device deployment system include one or more batteries, single use batteries, rechargeable batteries, capacitors, ultracapacitors, and any other energy storage device considered suitable for a particular embodiment.

As best illustrated in FIG. 5, the spring 91 has a first end 98*a* attached to the first pin 40*a* defined by the housing body 30 and a second end 98*b* that is coiled (e.g., coiled within a plane, wound or arranged in a spiral or sequence of rings). The first end 98*a* of the spring 91 is attached to the first pin 40*a* such that the spring 91 is moveable between a first configuration and a second configuration as the trigger 23 is moved between its first position and second position. In the embodiment illustrated, spring 91 is biased to the first configuration such that the trigger 23 is biased toward its first position. When the trigger 23 is in the first position the spring 91 is in the first configuration and when the trigger is in the second position the spring 91 is in the second configuration. In the first configuration, the spring 91 is free of contact with the third wire member 97. In the second configuration, the spring 91 contacts the third wire member 97. Thus, spring 91 acts as a switch in the illustrated powered medical device deployment system 10.

The spring 91 can comprise any suitable spring, can be formed of any suitable material, and can have any suitable structural arrangement, skilled artisans will be able to select a suitable material and structural arrangement for a spring according to a particular embodiment based on various considerations, including the material(s) that forms the housing and/or trigger of an embodiment. Example materials considered suitable to form a spring include metals, conductive materials, and any other material considered suitable for a particular embodiment. Example structural arrangements considered suitable for a spring include flat, round, and any other structural arrangement considered suitable for a particular embodiment.

The spring 91 can be attached to the first pin 40*a* using any suitable technique or method, and skilled artisans will be able to select a suitable technique or method to attach a spring to a pin according to a particular embodiment based on various considerations, including the material(s) that forms the pin. Example techniques and methods considered suitable to attach a spring to a pin include using adhesives, mechanical connections, threaded connections, welding, fusing (e.g., heat fusing), and any other technique or method considered suitable for a particular embodiment.

The motor 92 is disposed within the chamber 36 and is operatively attached to the sheath 20 via the drive axle 93 and the drive wheel 94. The motor 92 is in communication with the energy storage device 90 via the spring 91, the first wire member 95, the second wire member 96, and the third wire member 97, as described herein. In the illustrated embodiment, the motor 92 comprises a pancake motor that is attached to the housing 16 and is moveable between an on state and an off state. The motor 92 is in its on state when the trigger 23 is in its second position and the motor 92 is in its off state when the trigger 23 is in its first position. When the motor 92 is in the on state the motor 92 creates rotational movement and when the motor 92 is in the off state the motor 92 is static.

While the motor 92 has been described as a pancake motor, a motor included in a powered medical device deployment system can comprise any suitable motor. Skilled artisans will be able to select a suitable motor to include in a powered medical device deployment system according to a particular embodiment based on various considerations, including the amount of axial movement intended to be achieved by a sheath of an embodiment. Example motors considered suitable to include in a powered medical device deployment system include electric motors, printed circuit motors, pancake motors, printed armature motors, flat armature motors, variable speed motors, direct drive motors, and any other motor considered suitable for a particular embodiment. Alternatively, a motor can be disposed within a motor chamber defined by the housing. While the motor 92 has been illustrated as producing rotational movement, alternative embodiments can include linear motors that produce linear movement such that when the motor is in the on state the motor moves the sheath axially over the cannula. Optionally, a motor can comprise a variable speed motor that is configured to have an output power that varies. For example, the output power can be based on the amount of force applied to the trigger, the distance the trigger has been passed into the chamber defined by the housing, or the distance the sheath has been advanced over the cannula and/or medical device. For example, the motor can have a first output power when the trigger is in the first position, a second output power when the trigger is between the first position and the second position, and a third output power when the trigger is in the second position. The first output power is less than the second output power and the second output power is less than the third output power. This provides a mechanism for overcoming the initial force required to begin deployment of the medical device. Alternatively, the motor can have a first output power to initiate deployment of a medical device that is greater than a second output power that completes axial advancement of the sheath over the cannula and/or medical device. The first output power can be applied for a first interval of time and the second output power can be applied for a second interval of time. The second interval of time is greater than the first interval of time.

The motor 92 can optionally be calibrated such that when it is in the on state the force that is applied to the sheath 20 by the drive wheel 94 on an axis that is parallel to the lengthwise axis 11 of the powered medical device deployment system 10 is equal to a predetermined magnitude. For example, if the medical device 25 comprises a coated stent, the force required to advance the sheath 20 distally over the cannula 18 and the medical device 25 will be greater than embodiments in which the medical device 25 comprises a non-coated stent. Skilled artisans will be able to select a suitable axial force to apply to a sheath according to a particular embodiment based on various considerations, including the type of medical device being deployed. For example, a motor can be calibrated such that when it is in the on state the force that is applied to the sheath by the drive wheel on an axis that is parallel to the lengthwise axis of the powered medical device deployment system has a magnitude that is equal to, substantially equal to, greater than, or less than, 50 N, 60 N, 70 N, or and any other magnitude considered suitable for a particular embodiment.

The drive axle 93 is attached to the motor 92 and has a lengthwise axis 99. The drive axle 93 is attached to the motor 92 such that when the motor 92 is in the on state the drive axle 93 rotates counterclockwise about its lengthwise axis 99, which is disposed on a plane that extends at an angle relative to the lengthwise axis 11 of the powered medical device deployment system 10. In the embodiment illustrated, the lengthwise axis 99 of the drive axle 93 is disposed on a plane that is orthogonal to the lengthwise axis 11 of the powered medical device deployment system 10. However, alternative embodiments can include a drive axle that has a lengthwise axis that is disposed on a plane positioned at any suitable angle relative to the lengthwise axis of a powered medical device deployment system, such as 45 degrees, about 45 degrees, 135 degrees, about 135 degrees, and any other angle considered suitable for a particular embodiment. Depending on the structural arrangement of the motor relative to the sheath, alternative embodiments can be configured such that when the motor is in the on state the drive axle rotates clockwise about its lengthwise axis. Optionally, the drive wheel can comprise the output shaft of the motor.

As best illustrated in FIG. 8, the drive wheel 94 is attached to the drive axle 93 and is operatively attached to the motor 92. The drive wheel 94 has a drive wheel body 100 that defines a passageway 101 and a concave surface 102 about the circumference of the drive wheel 94. In the illustrated embodiment, the drive wheel 94 contacts the sheath 20 such that when the motor 92 is in the on state the drive wheel 94 transfers movement created by the motor 92 to the sheath 20. Thus, when the motor 92 is in the on state the drive wheel 94 rotates about the lengthwise axis 99 of the drive axle 93 such that the sheath 20 and the flush port 22 move axially on the cannula 18 and within the housing 16 and the axis 67 directed through the slot 35 defined by the housing 16 moves within the slot 35.

The drive wheel 94 can be formed of any suitable material, such as biocompatible materials, materials that can be made biocompatible, metals such as stainless steel, titanium, nickel-titanium alloys, polymers, polyethylene, polyvinyl chloride, polystyrene, and any other material considered suitable for a particular embodiment. Optionally, a drive wheel, or a portion of a drive wheel (e.g., concave surface 102), can be formed of a high friction material(s) (e.g., neoprene) such that a high coefficient of friction is created between the drive wheel and the sheath relative to embodiments that form a drive wheel of a low friction material(s). Optionally, a portion of the drive wheel (e.g., concave surface) can include a coating that increases the coefficient of friction between the drive wheel and the exterior surface of the sheath relative to embodiments that do not include a coating.

The first wire member 95 has a first end 106 attached to the energy storage device 90 and a second end 107 attached to the motor 92. Alternatively, the first wire member 95 can have a first end 106 that is in communication with the energy storage device 90 (e.g., via one or more conductive contacts). The second wire member 96 has a first end 108 attached to the energy storage device 90 and a second end 109 attached to the first pin 40a defined by the housing 16. The second end 109 of the second wire member 96 is attached to the first pin 40a such that it is connected to the spring 91 and in communication (e.g., electrical communication) with the spring 91. Alternatively, the second wire member 96 can have a first end 108 that is in communication with the energy storage device 90 (e.g., via one or more conductive contacts). The third wire member 97 has a first end 110 attached to the motor 92 and a second end 111 attached to the second pin 40b defined by the housing 16. Each of the first wire member 95, second wire member 96, and third wire member 97 can comprise any suitable wire member. In the embodiment illustrated, the first wire member 95, second wire member 96, and third wire member 97 have an inner conductor member with an insulation sheath disposed about its circumference.

Attachment of the first wire member 95 to the energy storage device 90 and the motor 92, attachment of the second wire member 96 to the energy storage device 90 and the first pin 40a and the spring 91, and attachment of the third wire member 97 to the second pin 40b and the motor 92 can be accomplished using any suitable technique or method, such as direct attachment, using terminals, connectors, contacts, conductive contacts, welding, soldering, and any other technique or method considered suitable for a particular embodiment.

The second end 111 of the third wire member 97 comprises an exposed portion of the inner conductor member (e.g., outer sheath has been removed) that is attached to the second pin 40b defined by the housing 16. When the trigger 23 is in the first position the spring 91 is free of contact with the third wire member 97 and when the trigger 23 is in the second position the spring 91 contacts the exposed portion of the third wire member 97 such that a complete electrical circuit 112 is formed between the energy storage device 90, the spring 91, the motor 92, the first wire member 95, the second wire member 96, and the third wire member 97. This is illustrated in FIG. 4. Thus, when the spring 91 is in the second configuration the motor 92 is operatively connected to the energy storage device 90.

The electrical circuit 112 illustrates an example of how an energy storage device 90 can be electrically connected to a motor 92. In the illustrated embodiment, the electrical circuit 112 comprises the energy storage device 90, the motor 92, the spring 91, the first wire member 95, the second wire member 96, and the third wire member 97. While the spring 91 has been illustrated as an example of a switch, any suitable switch can be included in a powered medical device deployment system, as described herein. The energy storage device 90 is connected to the motor 92 via the first wire member 95 and the spring 91 is connected to the energy storage device 90 via the second wire member 96 and to the motor 92 via the third wire member 97.

While a particular structural arrangement of elements has been illustrated to form a complete circuit 112, a circuit formed by one or more of the elements of a powered medical device deployment system can be structurally arranged in any suitable manner such that when a trigger is moved from its first position to its second position the circuit is complete. Skilled artisans will be able to select a suitable structural arrangement of elements to form a complete circuit according to a particular embodiment based on various considerations, such as the structural arrangement of the housing, trigger, and/or motor of a powered medical device deployment system. For example, alternative to using a spring that contacts an exposed portion of a wire member, the trigger of an embodiment can be attached to the motor using a wire member (e.g., third wire member) and can comprise an electrical contact that is positioned on the trigger such that when it is moved to its second position it contacts the spring or a portion of the second wire member to complete the circuit.

In the illustrated embodiment, the medical device 25 comprises an expandable intraluminal medical device that has a proximal end 114, a distal end 115, an axial length 116 that extends from the proximal end 114 to the distal end 115, and a medical device body 117 that defines a lumen 118. The medical device 25 is disposed on the cannula 18 such that the distal end 115 is disposed distal to the distal end 43 of the cannula 18. However, a medical device can be disposed at any suitable location on a cannula. For example, a medical device can be disposed on a cannula such that the distal end of the medical device is adjacent, or parallel with, the distal end of the cannula. Optionally, a powered medical device deployment system can omit the inclusion of a medical device.

Any suitable medical device can be included in a powered medical device deployment system, and skilled artisans will be able to select a suitable medical device to include in a powered medical device deployment system according to a particular embodiment based on various considerations, including the treatment intended to be performed. Examples of medical devices considered suitable to include in a powered medical device deployment system include expandable medical devices, stents, expandable stents, stents with biologically-active coatings, stents with attached grafts, including grafts of biological origin, and tissue-based prosthetic valve devices, such as prosthetic heart valves and prosthetic venous valves that include one or more section of tissue, tissue-derived material, or other flexible material.

In use, when the trigger 23 is in its first position, the idler wheel 72 is free of contact with the sheath 20, the spring 91 is in its first configuration and is free of contact with the third wire member 97, the motor 92 is in the off state, and the drive wheel 94 is static. Thus, when the trigger 23 is in the first position, the spring 91 is in the first configuration, the sheath 20 does not move relative to the cannula 18, and the medical device 25 is initially disposed between the cannula 18 and the sheath 20. This is illustrated in FIGS. 1 and 2.

When the trigger 23 is in its second position, the idler wheel 72 contacts the sheath 20, the spring 91 is in its second configuration and contacts the third wire member 97 such that a complete circuit 112 is formed, the motor 92 is in the on state, and the drive wheel 94 rotates about the lengthwise axis 99 of the drive axle 93. Thus, when the trigger 23 is in the second position, the sheath 20 moves axially over the cannula 18 in a distal direction such that the medical device 25 becomes exposed and can be delivered at a point of treatment. This is illustrated in FIGS. 3 and 4.

The trigger 23 provides a mechanism for deploying the medical device 25 in any suitable manner. For example, movement of the trigger 23 from the first position to the second position can be accomplished by applying a force on the trigger 23 that is directed toward the housing body 30. If the force being applied to the trigger 23 is maintained, the medical device 25 can be deployed in a single stage. Alternatively, if a force is applied to the trigger 23 at one or more intervals of time, the medical device 25 can be deployed in more than one stage. For example, a force can be applied to the trigger 23 for a first interval of time such that a first portion of the medical device 25 is exposed. The portion of the axial length 116 of the medical device 25 that is disposed distal to the distal end 49 of the sheath 20 can be determined by reviewing the location of the port 63 (e.g., second lumen 64, axis of second lumen 67) relative to the plurality of indicia 31 defined by the housing 16. A force can be applied to the trigger 23 for a second interval of time such that a second portion of the medical device 25 is exposed that is greater than the first portion. The portion of the axial length 116 of the medical device 25 that is disposed distal to the distal end 49 of the sheath 20 can be determined by reviewing the location of the port 63 (e.g., second lumen 64, axis of second lumen 67) relative to the plurality of indicia 31 defined by the housing 16. A force can be applied to the trigger 23 for a third interval of time such that a third portion of the medical device 25 is exposed that is greater than the second portion. The portion of the axial length 116 of the medical device 25 that is disposed distal to the distal end 49 of the sheath 20 can be determined by reviewing the location of the port 63 (e.g., second lumen 64, axis of second lumen 67) relative to the plurality of indicia 31 defined by the housing 16.

A force can be applied to a trigger 23 any suitable number of times and for any suitable interval of time to accomplish a staged deployment of the medical device 25, and skilled artisans will be able to select a suitable number of times to apply a force to a trigger and a suitable interval of time to apply each force according to a particular embodiment based on various considerations, including the treatment intended to be performed and/or the type of medical device being deployed. Example number of times a force can be applied to a trigger include one, at least one, two, a plurality, three, four, five, six, seven, eight, and any other number considered suitable for a particular embodiment. The interval of time that a force can be applied will be based on at least the output power (e.g., calibration) of the motor 92 and the structural arrangement of the drive wheel 94 included in the powered medical device deployment system 10 and can vary according to the staged deployment intended to be accomplished. For example, a first interval of time, a second interval of time, and/or a third interval of time can be equal to, or substantially equal to, a length of time that accomplishes axial movement of the sheath such that one quarter, one third, or one half of the medical device has been deployed.

Figure 9:
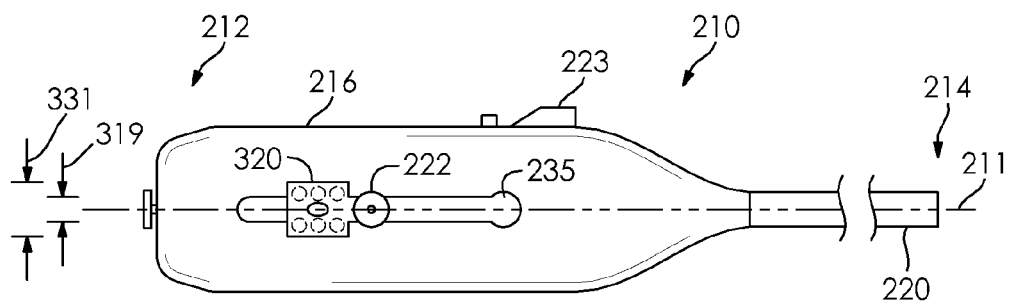
FIG. 9 is a side view of another embodiment of a powered medical device deployment system in an extended configuration.
Figure 9A:
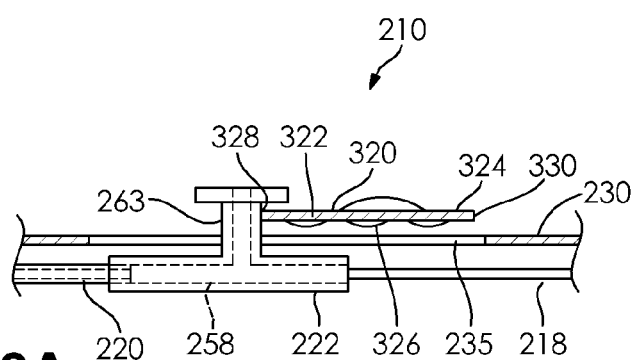
FIG. 9A is a partial cross-sectional view of the powered medical device deployment system illustrated in FIG. 9.

FIGS. 9 and 9A illustrate another embodiment of a powered medical device deployment system 210. Powered medical device deployment system 210 is similar to powered medical device deployment system 10 illustrated in FIGS. 1 through 8 and described above, except as detailed below. With respect to powered medical device deployment system 210, reference numbers in FIGS. 9 and 9A refer to the same structural element or feature referenced by the same number in FIGS. 1 through 8, offset by 200. Thus, powered medical device deployment system 210 has a housing 216, a cannula 218, a sheath 220, a flush port 222, and a trigger 223. The drive mechanism (e.g., drive mechanism 24) and medical device (e.g., medical device 25) have been omitted from the figures for clarity.

In the illustrated embodiment, the flush port body 258 defines a brake 320 that extends from the port 263 and toward the proximal end 212 of the powered medical device deployment system 210. The brake 320 comprises a brake body 322 that defines a shaft 324 and a plurality of protuberances 326.

The shaft 324 has a first end 328, a second end 330, and a width 331. The shaft 324 extends from the first end 328 toward the proximal end 212 of the powered medical device deployment system 210 to the second end 330. The width 331 of the shaft 324 is greater than the width 319 of the slot 235. The first end 328 of the shaft 324 is attached to the port 263 and the second end 330 of the shaft 324 is free of attachment to the port 263 such that the shaft 324 can move between a first position and a second position. In the first position the shaft 324 and each protuberance of the plurality of protuberances 326 are free of contact with the housing body 230 and in the second position at least one protuberance of the plurality of protuberances 326 is in contact with the housing body 230. However, alternative embodiments can include a shaft that is moveable to a second position such that at least a portion of the shaft or more than one, at least two, a plurality, or all of the protuberances of the plurality of protuberances are in contact with the housing body.

Each protuberance of the plurality of protuberances 326 extends from the shaft 324 and toward the housing 216 and comprises a high friction material such that each protuberance of the plurality of protuberances 326 has a coefficient of friction between the protuberance and the housing body 230 that is greater than the coefficient of friction between the flush port body 258 and the housing body 230. Thus, the flush port 222 has a first coefficient of friction between a protuberance of the plurality of protuberances 326 and the housing 216 and a second coefficient of friction between the flush port body 258 and the housing 216. The first coefficient of friction is greater than the second coefficient of friction.

Each protuberance of the plurality of protuberances 326 can be formed of any suitable high friction material, and skilled artisans will be able to select a suitable high friction material according to a particular embodiment based on various considerations, including the material(s) that forms the housing of an embodiment. Example high friction materials considered suitable include rubber, neoprene, and any other material considered suitable for a particular embodiment. Alternative to forming each protuberance of the plurality of protuberances as a portion of the brake 320, a protuberance can comprise a separate element that is attached to the shaft of a brake using any suitable technique or method, such as using adhesives or welding.

During use, the application of a force on the shaft 324 toward the housing 216 moves the shaft 324 from its first position to its second position such that at least one of the plurality of protuberances 326 contacts the housing body 230 and prevents, or stops, movement of the sheath 220 over the cannula 218. Therefore, the brake 320 provides a mechanism for preventing, or stopping, movement of the sheath 220 over the cannula 218.

While the brake 320 has been illustrated as having a particular structural arrangement, extending toward the proximal end of the powered medical device deployment system, and as being disposed between the first end and the second end of the port, a brake can have any suitable structural arrangement, extend in any suitable direction, and can be positioned at any suitable location on a port. Skilled artisans will be able to select a suitable structural arrangement for a brake according to a particular embodiment based on various considerations, including the structural arrangement of a housing. For example, a brake can extend toward the distal end of a housing, be positioned at the second end of a port that is disposed outside of the housing, and/or extend along one side of the slot defined by the housing.

While a plurality of protuberances 326 has been illustrated, a brake can include any suitable number of protuberances, and skilled artisans will be able to select a suitable number of protuberances to include on a brake according to a particular embodiment based on various considerations, including the amount of friction intended to be applied on a housing when a force is applied to the shaft of a brake. Example number of protuberances considered suitable to include on a brake include one, at least one, two, a plurality, three, four, five, six, seven, eight, and any other number considered suitable for a particular embodiment. Alternative to, or in combination with, including a plurality of protuberances, a coating of a high friction material can be applied to the surface of the shaft of a brake that is directed toward the housing and/or the surface of the housing that is able to contact the shaft of a brake.

Figure 10:
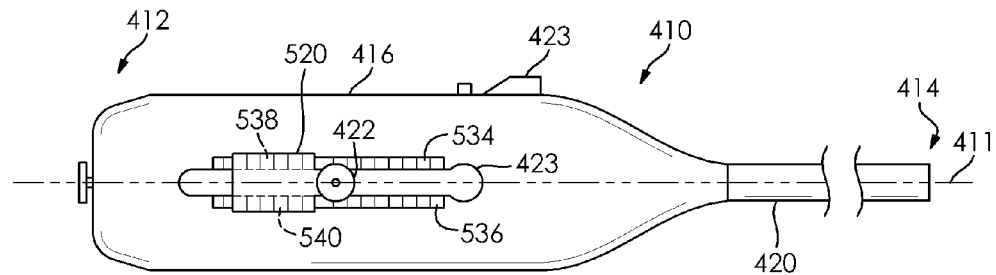
FIG. 10 is a side view of another embodiment of a powered medical device deployment system in an extended configuration.
Figure 10A:
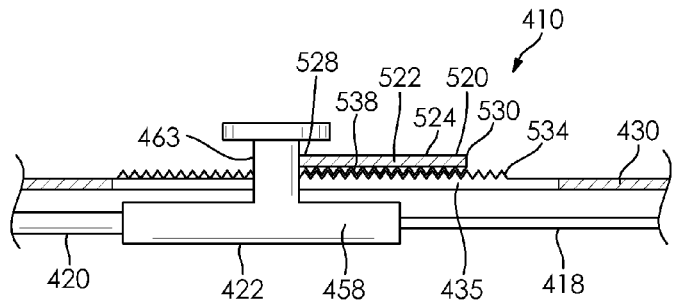
FIG. 10A is a partial cross-sectional view of the powered medical device deployment system illustrated in FIG. 10.

FIGS. 10 and 10A illustrate another embodiment of a powered medical device deployment system 410. Powered medical device deployment system 410 is similar to powered medical device deployment system 210 illustrated in FIGS. 9 and 9A and described above, except as detailed below. With respect to powered medical device deployment system 410, reference numbers in FIGS. 10 and 10A refer to the same structural element or feature referenced by the same number in FIGS. 9 and 9A, offset by 200. Thus, powered medical device deployment system 410 has a housing 416, a cannula 418, a sheath 420, a flush port 422, and a trigger 423. The drive mechanism (e.g., drive mechanism 24) and medical device (e.g., medical device 25) have been omitted from the figures for clarity.

In the illustrated embodiment, the housing body 430 defines a first toothed geometry 534 and a second toothed geometry 536. Each of the first toothed geometry 534 and the second toothed geometry 536 is disposed adjacent to the slot 435, extends along a portion of the length of the slot 435, and is sized and configured to receive a portion of the first toothed geometry 538 and second toothed geometry 540 defined by the shaft 524 of the brake 520, as described in more detail herein. Alternative to the embodiment illustrated, a first toothed geometry and/or a second toothed geometry defined by the housing body can extend along the entire axial length of the slot, or a distance that is greater than the axial length of the slot.

In the illustrated embodiment, alternative to defining a plurality of protuberances (e.g., plurality of protuberances 326), the brake body 522 defines a first toothed geometry 538 and a second toothed geometry 540. Each of the first toothed geometry 538 and the second toothed geometry 540 extends toward the housing 416, is disposed adjacent to the slot 435, extends along a portion of the length of the shaft 524, and is sized and configured to receive a portion of the first toothed geometry 534 and second toothed geometry 536 defined by the housing 416. Alternative to the embodiment illustrated, a first toothed geometry and/or a second toothed geometry defined by the brake body can extend along the entire axial length of the shaft.

During use, the application of a force on the shaft 524 toward the housing 416 moves the shaft 524 from its first position to its second position. In the second position, a portion of the first toothed geometry 534 defined by the housing 416 engages a portion of the first toothed geometry 538 defined by the brake 520 and a portion of the second toothed geometry 536 defined by the housing 416 engages a portion of the second toothed geometry 540 defined by the brake 520. In the second position, the brake 520 prevents, or stops, movement of the sheath 420 over the cannula 418. Therefore, the brake 520 provides a mechanism for preventing, or stopping, movement of the sheath 420 over the cannula 418.

While the powered medical device deployment system 410 has been illustrated as having a particular structural arrangement and including first and second toothed geometries 534, 536 on the housing 416 and first and second toothed geometries 538, 540 on the brake 520, a powered medical device can include any suitable structural configuration capable of providing a mechanism to prevent, or stop, advancement of a sheath over a cannula. Skilled artisans will be able to select suitable structure to include on a powered medical device deployment system according to a particular embodiment based on various considerations, including the material(s) that forms the housing and/or the brake. For example, the housing can include only a first toothed geometry and the shaft of a brake can include only a first toothed geometry.

Figure 11:
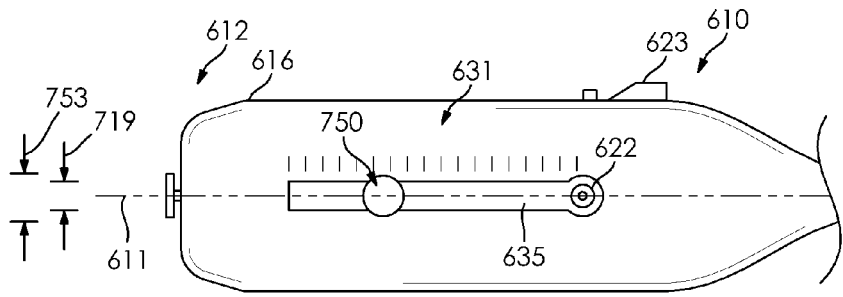
FIG. 11 is a partial side view of the powered medical device deployment system illustrated in FIG. 1 with an associated mechanical stop.
Figure 11A:
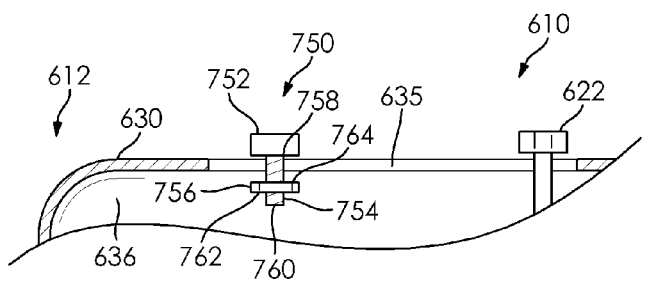
FIG. 11A is a partial cross-sectional view of the powered medical device deployment system illustrated in FIG. 11.

FIGS. 11 and 11A illustrate another embodiment of a powered medical device deployment system 610. Powered medical device deployment system 610 is similar to powered medical device deployment system 10 illustrated in FIGS. 1 through 8 and described above, except as detailed below. With respect to the powered medical device deployment system 610, reference numbers in FIGS. 11 and 11A refer to the same structural element or feature referenced by the same number in FIGS. 1 through 8, offset by 600. Thus, the powered medical device deployment system 610 has a housing 616, a flush port 622, and a trigger 623. The cannula (e.g., cannula 18), sheath (e.g., sheath 20), drive mechanism (e.g., drive mechanism 24), and medical device (e.g., medical device 25) have been omitted from the figures for clarity.

In the illustrated embodiment, the powered medical device deployment system 610 includes a mechanical stop 750 partially disposed within the slot 635 defined by the housing 616. The mechanical stop 750 has a head 752, a threaded shaft 754, and a plate 756. The mechanical stop 750 is moveable between a first configuration and a second configuration.

The head 752 is disposed outside of the chamber 636 defined by the housing 616 and has a diameter 753 that is greater than the width 719 of the slot 635 such that the head 752 is unable to pass through the slot 635 and into the chamber 636. The threaded shaft 754 extends from the head 752, through the slot 635 defined by the housing 616, and into the chamber 636. The threaded shaft 754 has a first end 758 attached to the head 752 and a second end 760 that is disposed within the chamber 636.

The plate 756 has a plate body 762 that defines an aperture 764 and is moveably attached to the threaded shaft 754 between a first position and a second position. In the first position the plate 756 is a first distance from the head 752. In the second position the plate 756 is a second distance from the head 752 that is less than the first distance. The plate body 762 defines threads about the circumference of the aperture 764 that are sized and configured to engage with the threads defined by the threaded shaft 754. The aperture 764 has an inside diameter that is less than the outside diameter of the second end 760 of the threaded shaft 754. This prevents the plate 756 from becoming separated from the mechanical stop 750.

In use, a user determines the length of the medical device that is desired to be deployed. For example, if a staged deployment is desired, a first length of the medial device can be deployed in a first stage. The first length can be located on the slot 635 relative to an indicium of the plurality of indicia 631 and the mechanical stop 750 can be positioned adjacent to the first length. A rotational force can then be applied to the head 752 in a first direction such that the threads defined by the threaded shaft 754 engage the threads defined by the plate body 762 and the plate 752 advances toward the head 752. The rotational force is applied on the head 752 until the head 752 contacts the housing body 630 (e.g., exterior surface of the housing 616) and the plate 756 contacts the housing body 630 (e.g., interior surface of housing 616). The rotational force can be applied until the mechanical stop 750 is releasably fixed in the desired location. This provides a mechanism for preventing movement of the sheath beyond the location of the mechanical stop 750 such that a desired length of the medical device can be deployed.

To remove, or adjust the position of the mechanical stop 750, a rotational force can be applied in second direction that is opposite that of the first direction, such that the threads defined by the threaded shaft 754 that are engaged with the threads defined by the plate body 762 advance the plate away from the head 752. The rotational force is applied on the head 752 until the mechanical stop 750 is free to move along the axial length of the slot 635 (e.g., the head is free of contact with the housing body 630 and/or the plate 756 is free of contact with the housing body 630).

Figure 12:
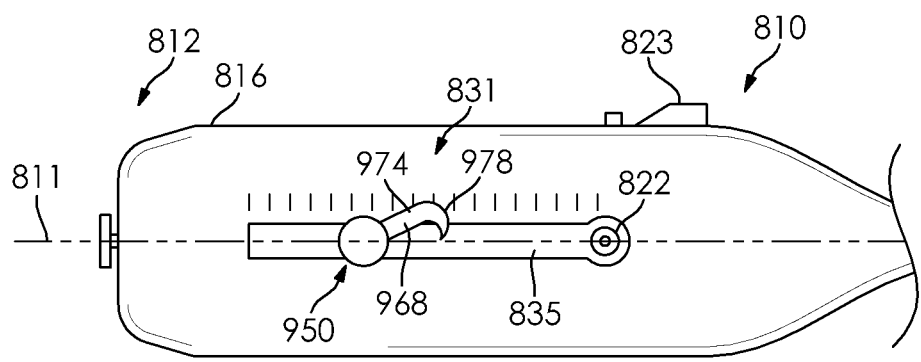
FIG. 12 is a side view of the powered medical device deployment system illustrated in FIG. 1 with another associated mechanical stop.
Figure 12A:
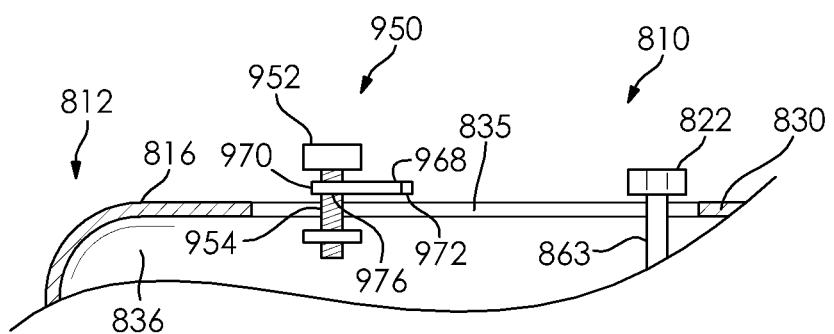
FIG. 12A is a partial cross-sectional view of the powered medical device deployment system illustrated in FIG. 12.

FIGS. 12 and 12A illustrate another embodiment of a powered medical device deployment system 810. Powered medical device deployment system 810 is similar to powered medical device deployment system 610 illustrated in FIGS. 11 and 11A and described above, except as detailed below. With respect to powered medical device deployment system 810, reference numbers in FIGS. 12 and 12A refer to the same structural element or feature referenced by the same number in FIGS. 11 and 11A, offset by 200. Thus, powered medical device deployment system 810 has a housing 816, a flush port 822, and a trigger 823. The cannula (e.g., cannula 18), sheath (e.g., sheath 20), drive mechanism (e.g., drive mechanism 24), and medical device (e.g., medical device 25) have been omitted from the figures for clarity.

In the illustrated embodiment, the mechanical stop 950 includes an attachment mechanism 968 that is disposed between the head 952 and the exterior surface of the housing 816. The attachment mechanism 968 has a first end 970, a second end 972, and a attachment mechanism body 974 that defines an aperture 976 and a curve 978. The attachment mechanism 968 is moveable between a first position and a second position. The aperture 976 is defined between the first end 970 and the second end 972 and is sized and configured to receive a portion of the threaded shaft 954. The attachment mechanism body 974 defines the curve 978 between the aperture 976 and the second end 972. The curve 978 is sized and configured to receive a portion of the flush port 822. In the embodiment illustrated, the curve 978 is sized and configured to receive a portion of the port 863 (e.g., the curve 978 has a radius of curvature that corresponds to the radius of curvature of the port 863).

In the first position, the attachment mechanism 968 is free of contact with the port 863 such that the port 863 can move within the slot 835 and the sheath can move axially over the cannula. In the second position, the attachment mechanism 968 is disposed over the port 863 such that the port 863 is disposed between the curve 978 and the head 952. This provides a mechanism for manually advancing the sheath over the cannula (e.g., attachment mechanism 968 provides a bailout feature to the system).

Figure 13:
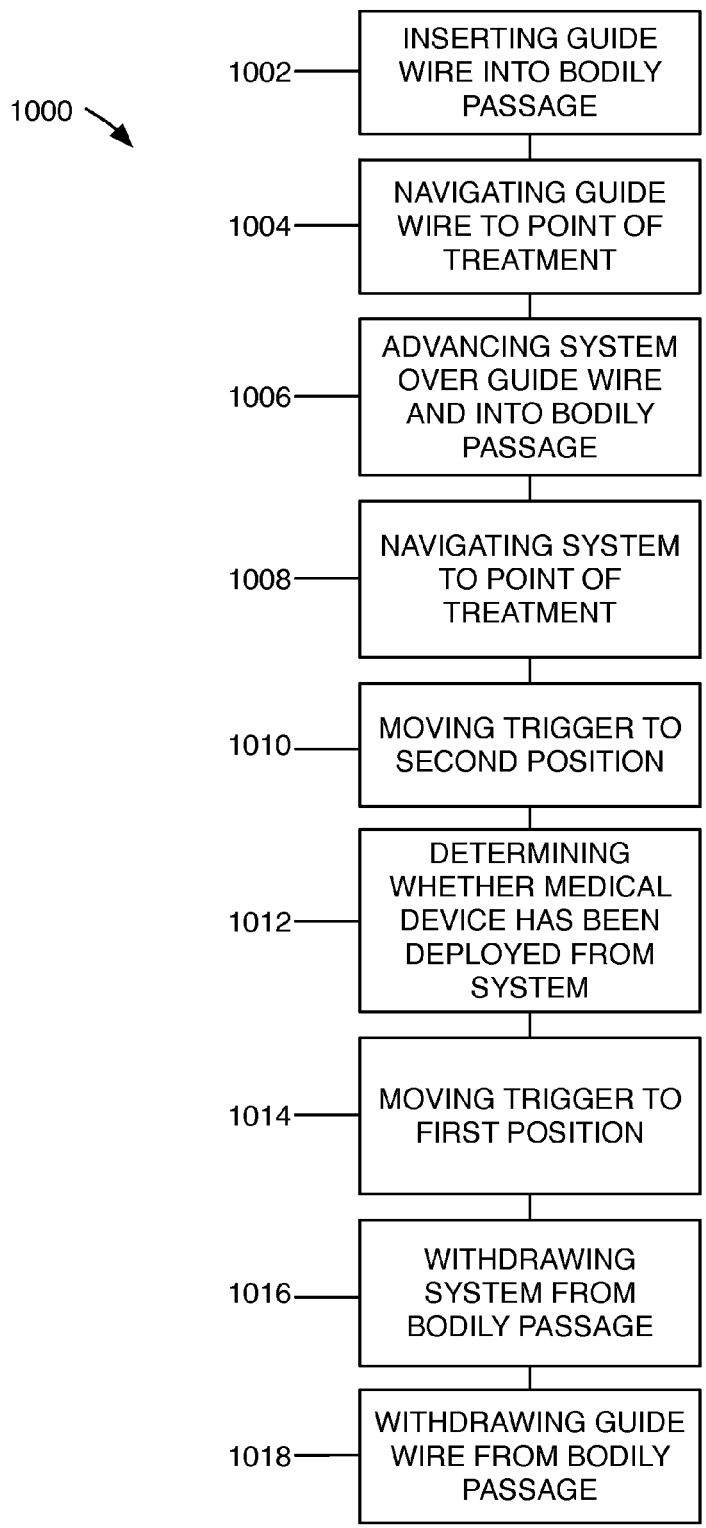
FIG. 13 is a flowchart representation of a method of treatment using a powered medical device deployment system.

FIG. 13 is a flowchart representation of a method of treatment 1000 using a powered medical device deployment system.

A step 1002 comprises inserting a guide wire having a proximal end and a distal end into a bodily passage such that the distal end of the guide wire is disposed within the bodily passage. Another step 1004 comprises navigating the distal end of the guide wire to a point of treatment within the bodily passage. Another step 1006 comprises advancing a powered medical device deployment system having a proximal end and a distal end over the previously placed guide wire such that the distal end of the powered medical device deployment system is disposed within the bodily passage. The powered medical device deployment system comprises a housing, a cannula, a sheath, a flush port, a trigger, a drive mechanism, and a medical device. Another step 1008 comprises navigating the distal end of the powered medical device deployment system distal to the point of treatment within the bodily passage. Another step 1010 comprises moving the trigger from the first position to the second position such that the drive mechanism moves from the off state to the on state and the sheath axially advances in a distal direction over the cannula. This results in deployment of the medical device at the point of treatment. Another step 1012 comprises determining whether the medical device has been deployed from the powered medical device deployment system. Another step 1014 comprises moving the trigger from the second position to the first position. Another step 1016 comprises withdrawing the powered medical device deployment system from the bodily passage. Another step 1018 comprises withdrawing the guide wire from the bodily passage.

Step 1002 can be accomplished by applying a distally-directed force on any suitable portion of the guide wire such that the distal end of the guide wire is disposed within the bodily passage. Step 1002 can be accomplished using a guide wire that has any suitable length, structural configuration, and that is formed of any suitable material.

Step 1004 can be accomplished by applying a distally-directed force on any suitable portion of the guide wire such that the distal end of the guide wire is disposed distal to a point of treatment. Alternatively, step 1004 can be accomplished such that the distal end of the guide wire is disposed near, adjacent, proximal to, or at a point of treatment. Optionally step 1004 can be accomplished using any suitable visualization technique, and skilled artisans will be able to select a suitable visualization technique to determine the location of the distal end of a wire guide within a bodily passage according to a particular embodiment based on various considerations, including the treatment intended to be performed. Example visualization techniques considered suitable include x-ray, fluoroscopy, ultrasound, direct visualization with a scope, magnetic resonance imaging, and any other visualization technique considered suitable for a particular embodiment. An optional step comprises confirming placement of the distal end of the guide wire using any suitable visualization technique, such as those described herein. Optionally, steps 1002 and 1004 can be omitted in methods that do not require the use of a guide wire.

Step 1006 can be accomplished by applying a distally-directed force on any suitable portion of a powered medical device deployment system (e.g., housing). Step 1006 can be accomplished using any suitable powered medical device deployment system, and skilled artisans will be able to select a suitable powered medical device deployment system to use in a method of treatment according to a particular embodiment based on various considerations, including the location of the point of treatment, and/or the type of medical device being delivered at the point of treatment. Example powered medical device deployment systems considered suitable to use in a method of treatment include the powered medical device deployment systems described herein, such as powered medical device deployment system 10, powered medical device deployment system 210, powered medical device deployment system 410, powered medical device deployment system 610, powered medical device deployment system 810, variations thereof, and any other powered medical device deployment system considered suitable for a particular method of treatment. An exemplary powered medical device deployment system that can be used to accomplish the methods, steps, alternative steps, and/or optional steps described herein is illustrated and described with respect to FIGS. 1 through 8, and comprises a housing 16, a cannula 18, a sheath 20, a flush port 22, a trigger, 23, a drive mechanism 24, and a medical device 25.

Step 1006 can be accomplished by inserting the proximal end of the guide wire through the lumen 46 defined by the cannula 18 and applying a distally-directed force on the powered medical device deployment system 10 until the distal end 14 of the powered medical device deployment system 10 is disposed within the bodily passage.

In embodiments in which a guide wire is not used to complete a method of treatment, an alternative step comprises introducing a powered medical device deployment system into a bodily passage such that the distal end of the powered medical device deployment system is disposed within the bodily passage.

Step 1008 can be accomplished by applying a distally-directed force on any suitable portion of the powered medical device deployment system 10 such that the distal end 14 of the powered medical device deployment system 10 is disposed distal to the point of treatment within the bodily passage. Step 1008 is accomplished such that the medical device 25 is disposed within the bodily passage at, or adjacent to, the point of treatment (e.g., the location the medical device is intended to be deployed).

Alternatively, step 1008 can be accomplished such that the distal end 14 of the powered medical device deployment system 10 is disposed near, proximal to, or at a point of treatment within the bodily passage. Optionally step 1008 can be accomplished using any suitable visualization technique, such as those described herein. For example, an optional step that can be completed concurrently with, or subsequent to, the step of navigating the distal end of the powered medical device deployment system to a point of treatment within the bodily passage comprises confirming placement of the powered medical device deployment system within the bodily passage such that the medical device is disposed adjacent to, or substantially adjacent to, proximal to, distal to, or near, the point of treatment. This optional step can be accomplished using any suitable visualization technique, such as those described herein. Optionally, step 1004 and step 1008 can be accomplished concurrently.

Step 1010 can be accomplished by applying a force on the trigger that is directed toward the housing of the powered medical device deployment system. In embodiments in which the trigger of the powered medical device deployment system includes a safety release, an optional step that can be completed prior to step 1010 comprises moving the safety release from the first position to the second position. This optional step can be accomplished by applying a distally-directed force on the protuberance of the safety release such that it the safety release becomes free of the recess defined by the housing.

In embodiments in which the flush port of the powered medical device deployment system includes a brake, an optional step comprises moving the brake from the first position to the second position such that movement of the sheath over the cannula has been stopped. This optional step can be accomplished by applying a force directed toward the housing on the brake of the flush port such that a portion of the brake (e.g., protuberance, toothed geometry) contacts the housing.

In embodiments in which the powered medical device deployment system includes a mechanical stop, an optional step comprises positioning the mechanical stop along the axial length of the slot defined by the housing at a location in which it is desired to stop axial movement of the sheath over the cannula. For example, if staged deployment of the medical device is desired, an optional step comprises positioning the mechanical stop at a first location between the proximal end and the distal end of the slot. This can be accomplished by positioning the mechanical stop relative to an indicium of the plurality of indicia disposed on the housing. Another optional step comprises moving the mechanical stop from its first configuration to its second configuration such that it is releasably attached to the housing. This can be accomplished by applying a rotational force to the head of the mechanical stop in a first direction. Subsequently, step 1010, step 1012, and/or step 1014 can be completed such that the sheath has been advanced distally over the cannula and a first portion of the medical device is disposed distal to the distal end of the sheath. Another optional step comprises moving the mechanical stop from its second configuration to its first configuration such that it is moveable within the slot. This can be accomplished by applying a rotational force to the head of the mechanical stop in a second direction that is opposite the first direction. Depending on the number of stages intended to be completed, another optional step comprises positioning the mechanical stop at a second location between the first location and the proximal end of the slot. This can be accomplished by advancing the mechanical stop proximally within the slot defined by the housing and positioning the mechanical stop relative to another indicium of the plurality of indicia disposed on the housing. Another optional step comprises moving the mechanical stop from its first configuration to its second configuration such that it is releasably attached to the housing. This can be accomplished by applying a rotational force to the head of the mechanical stop in the first direction. Subsequently, step 1010, step 1012, and/or step 1014 can be repeated such that the sheath has been advanced distally over the cannula and a second portion of the medical device that is greater in length than the first portion is disposed distal to the distal end of the sheath. These optional steps can be repeated any suitable number of times based on the staged deployment being accomplished.

Step 1012 can be accomplished by determining the position of the port 63 (e.g., second lumen 64, axis of second lumen 67) relative to the location of a predetermined indicium of the plurality of indicia disposed on the housing. The predetermined indicium of the plurality of indicia being a length that the sheath 20 must be retracted from the cannula 18 to achieve delivery of the medical device 25. If the port is not adjacent the predetermined indicium of the plurality of indicia, or disposed proximal to the predetermined indicium of the plurality of indicia, then the medical device has not been deployed from the powered medical device deployment system. If the port is adjacent the predetermined indicium of the plurality of indicia, or is disposed proximal to the predetermined indicium of the plurality of indicia, the medical device has been deployed from the powered medical device deployment system. An optional step comprises determining the length that the sheath must be axially advanced over the cannula in a distal direction to free the medical device from the powered medical device deployment system. Another optional step comprises locating that length on the plurality of indicia disposed on the housing such that a predetermined indicium of the plurality of indicium can be selected.

Step 1014 can be accomplished by removing the force being applied on the trigger of the powered medical device deployment system. An optional step comprises continuing step 1012 until the port is adjacent, or proximal to, a predetermined indicium of the plurality of indicia disposed on the housing.

Step 1016 can be accomplished by applying a proximally-directed force on any suitable portion of the powered medical device deployment system 10 (e.g., housing 16) such that it is advanced proximally over the guide wire and the distal end 14 is disposed outside of the bodily passage. Alternatively, if the distal end of the powered medical device deployment system has been navigated to a point of treatment independent of a guide wire, the step of withdrawing the distal end of the powered medical device deployment system from the bodily passage can be accomplished by applying a proximally-directed force on any suitable portion of the powered medical device deployment system until the distal end of the powered medical device deployment system is disposed outside of the bodily passage.

Step 1018 can be accomplished by applying a proximally-directed force on any suitable portion of the guide wire such that it is advanced proximally and is disposed outside of the bodily passage. Optionally, this step can be accomplished in combination with step 1016. Optionally, step 1018 can be omitted in methods in which the inclusion of a guide wire has been omitted.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A powered medical device deployment system comprising:
    a housing having a housing body defining a chamber and a slot, the slot providing access to the chamber;
    a cannula partially disposed within the chamber and having a cannula body that defines a cannula lumen extending through the cannula;
    a sheath slidably disposed over the cannula and partially disposed within the chamber, the sheath having a sheath body defining a sheath lumen extending through the sheath;
    a flush port attached to the sheath and having a flush port body that defines a flush port lumen in communication with the sheath lumen, the flush port lumen disposed on an axis extending through the slot defined by the housing;
    an electrical circuit disposed within the chamber and comprising an energy storage device, a motor connected to the energy storage device, and a switch connected to the energy storage device and adapted to connect to the motor, the energy storage device configured to store energy, the motor operatively attached to the sheath and moveable between an on state and an off state such that when the motor is in the on state the sheath and the flush port move axially over the cannula, the switch having a first configuration and a second configuration such that when the switch is in the first configuration the motor is in the off state and when the switch is in the second configuration the stored energy is supplied to the motor and the motor is in the on state; and
    a trigger partially disposed within the chamber and moveable between a first position and a second position, the trigger configured to move the switch between its first configuration and second configuration such that when the trigger is in the first position the switch is in the first configuration and when the trigger is in the second position the switch is in the second configuration.

2. The powered medical device deployment system of claim 1, further comprising a drive wheel operatively attached to the motor and contacting the sheath.

3. The powered medical device deployment system of claim 1, wherein the motor is a pancake motor.

4. The powered medical device deployment system of claim 1, wherein the switch comprises a spring attached to the housing and moveable between a first configuration and a second configuration, the spring contacting the trigger and biased to the first configuration.

5. The powered medical device deployment system of claim 1, wherein the housing further comprises one or more indicia disposed adjacent the slot defined by the housing.

6. The powered medical device deployment system of claim 1, wherein the trigger includes a safety release that is moveable between a first position and a second position such that when the safety release is in the first position the safety release prevents movement of the trigger between the first position and the second position and when the safety release is in the second position the trigger can move between the first position and the second position.

7. The powered medical device deployment system of claim 1, wherein the flush port has a guide member and a port, the guide member is slidably disposed over the cannula, the port extending from the guide member and through the slot defined by the housing.

8. The powered medical device deployment system of claim 7, wherein the flush port has a brake, the brake having a brake body and a plurality of protuberances, the brake body defining a shaft extending from the port and moveable between a first position and a second position such that when the shaft is in the first position it is free of contact with the housing and when the shaft is in the second position a portion of the shaft contacts the housing, the plurality of protuberances disposed on the shaft, each protuberance of the plurality of protuberances extending toward the housing and comprising a high friction material.

9. The powered medical device deployment system of claim 7, wherein the housing body defines a toothed geometry adjacent the slot; and
 wherein the flush port has a brake, the brake having a brake body defining a shaft and a toothed geometry, the shaft extending from the port and moveable between a first position and a second position such that when the shaft is in the first position it is free of contact with the housing and when the shaft is in the second position a portion of the shaft contacts the housing, the toothed geometry defined on the shaft and extending toward the housing, the toothed geometry defined by the brake body sized and configured to engage with the toothed geometry defined by the housing body.

10. The powered medical device deployment system of claim 1, further comprising a mechanical stop disposed within the slot defined by the housing, the mechanical stop moveable between a first configuration and a second configuration and comprising a head, a threaded shaft, and a plate, the head disposed outside of the chamber defined by the housing, the threaded shaft attached to the head and extending from the head through the slot and into the chamber defined by the housing, the plate moveably attached to the threaded shaft, in the first configuration the mechanical stop is moveable within the slot defined by the housing, in the second configuration the mechanical stop is releasably attached to the housing.

11. A powered medical device deployment system comprising:
 a housing having a housing body defining a chamber and a slot, the slot providing access to the chamber;
 a cannula partially disposed within the chamber and having a cannula body that defines a cannula lumen extending through the cannula;
 a sheath slidably disposed over the cannula and partially disposed within the chamber, the sheath having a sheath body defining a sheath lumen extending through the sheath;
 a flush port attached to the sheath and having a flush port body that defines a flush port lumen in communication with the sheath lumen, the flush port lumen disposed on an axis extending through the slot defined by the housing;
 an electrical circuit disposed within the chamber and comprising an energy storage device, a motor connected to the energy storage device, and a switch connected to the energy storage device and adapted to connect to the motor, the energy storage device configured to store energy, the motor operatively attached to the sheath and moveable between an on state and an off state such that when the motor is in the on state the sheath and the flush port move axially over the cannula, the switch having a first configuration and a second configuration such that when the switch is in the first configuration the motor is in the off state and when the switch is in the second configuration the stored energy is supplied to the motor and the motor is in the on state; and
 a trigger partially disposed within the chamber and moveable between a first position and a second position, the trigger configured to move the switch between its first configuration and second configuration such that when the trigger is in the first position the switch is in the first configuration and when the trigger is in the second position the switch is in the second configuration;
 wherein the trigger further comprises an idler wheel attached to the trigger such that when the trigger is in the first position the idler wheel is free of contact with the sheath and when the trigger is in the second position the idler wheel contacts the sheath.

12. A powered medical device deployment system comprising:
 a housing having a housing body defining a chamber and a slot providing access to the chamber;
 a cannula partially disposed within the chamber and having a cannula body that defines a cannula lumen extending through the cannula;
 a sheath slidably disposed over the cannula and partially disposed within the chamber, the sheath having a sheath body defining a sheath lumen extending through the sheath;
 a flush port attached to the sheath and having a flush port body that defines a flush port lumen in communication with the sheath lumen, the flush port lumen disposed on an axis extending through the slot defined by the housing;
 an electrical circuit disposed within the chamber and comprising an energy storage device, a motor connected to the energy storage device, and a switch connected to the energy storage device and adapted to connect to the motor, the energy storage device configured to store energy, the motor operatively attached to the sheath and moveable between an on state and an off state such that when the motor is in the on state the sheath and the flush port move axially over the cannula, the switch having a first configuration and a second configuration such that when the switch is in the first configuration the motor is in the off state and when the switch is in the second configuration the stored energy is supplied to the motor and the motor is in the on state;
 a drive wheel operatively attached to the motor and contacting the sheath; and
 a trigger partially disposed within the chamber and moveable between a first position and a second position, the trigger comprising an idler wheel and configured to move the switch between its first configuration and second configuration such that when the trigger is in the first position the switch is in the first configuration and when the trigger is in the second position the switch is in the second configuration, the idler wheel attached to the trigger such that when the trigger is in the first position the idler wheel is free of contact with the sheath and when the trigger is in the second position the idler wheel contacts the sheath.

13. The powered medical device deployment system of claim 12, wherein the motor is a pancake motor.

14. The powered medical device deployment system of claim 12, wherein the switch comprises a spring attached to the housing and moveable between a first configuration and a second configuration, the spring contacting the trigger and biased to the first configuration.

15. The powered medical device deployment system of claim 12, wherein the trigger includes a safety release that is moveable between a first position and a second position such that when the safety release is in the first position the safety release prevents movement of the trigger between the first position and the second position and when the safety release is in the second position the trigger can move between the first position and the second position.

16. The powered medical device deployment system of claim 12, wherein the flush port has a guide member and a port, the guide member is slidably disposed over the cannula, the port extending from the guide member and through the slot defined by the housing.

17. The powered medical device deployment system of claim 16, wherein the flush port has a brake, the brake having a brake body and a plurality of protuberances, the brake body defining a shaft extending from the port and moveable between a first position and a second position such that when the shaft is in the first position it is free of contact with the housing and when the shaft is in the second position a portion of the shaft contacts the housing, the plurality of protuberances disposed on the shaft, each protuberance of the plurality of protuberances extending toward the housing and comprising a high friction material.

18. The powered medical device deployment system of claim 16, wherein the housing body defines a toothed geometry adjacent the slot; and
wherein the flush port has a brake, the brake having a brake body defining a shaft and a toothed geometry, the shaft extending from the port and moveable between a first position and a second position such that when the shaft is in the first position it is free of contact with the housing and when the shaft is in the second position a portion of the shaft contacts the housing, the toothed geometry defined on the shaft and extending toward the housing, the toothed geometry defined by the brake body sized and configured to engage with the toothed geometry defined by the housing body.

19. The powered medical device deployment system of claim 12, further comprising a mechanical stop disposed within the slot defined by the housing, the mechanical stop moveable between a first configuration and a second configuration and comprising a head, a threaded shaft, and a plate, the head disposed outside of the chamber defined by the housing, the threaded shaft attached to the head and extending from the head through the slot and into the chamber defined by the housing, the plate moveably attached to the threaded shaft, in the first configuration the mechanical stop is moveable within the slot defined by the housing, in the second configuration the mechanical stop is releasably attached to the housing.

20. A powered medical device deployment system comprising:
a housing having a housing body defining a chamber and a slot providing access to the chamber;
a cannula partially disposed within the chamber and having a cannula body that defines a cannula lumen extending through the cannula;
a sheath slidably disposed over the cannula and partially disposed within the chamber, the sheath having a sheath body defining a sheath lumen extending through the sheath;
a flush port attached to the sheath and having a flush port body that defines a flush port lumen in communication with the sheath lumen, the flush port lumen disposed on an axis extending through the slot defined by the housing;
an electrical circuit disposed within the chamber and comprising an energy storage device, a pancake motor connected to the energy storage device, and a switch connected to the energy storage device and adapted to connect to the pancake motor, the energy storage device configured to store energy, the pancake motor operatively attached to the sheath and moveable between an on state and an off state such that when the pancake motor is in the on state the sheath and the flush port move axially over the cannula, the switch having a first configuration and a second configuration such that when the switch is in the first configuration the pancake motor is in the off state and when the switch is in the second configuration the stored energy is supplied to the pancake motor and the pancake motor is in the on state;
a drive wheel operatively attached to the pancake motor and contacting the sheath; and
a trigger partially disposed within the chamber and moveable between a first position and a second position, the trigger comprising an idler wheel, a safety release, and configured to move the switch between its first configuration and second configuration such that when the trigger is in the first position the switch is in the first configuration and when the trigger is in the second position the switch is in the second configuration, the idler wheel attached to the trigger such that when the trigger is in the first position the idler wheel is free of contact with the sheath and when the trigger is in the second position the idler wheel contacts the sheath, the safety release moveable between a first position and a second position such that when the safety release is in the first position the safety release prevents movement of the trigger between the first position and the second position and when the safety release is in the second position the trigger can move between the first position and the second position.

* * * * *